ated under 35
United States Patent
Yu et al.

(10) Patent No.: US 7,801,265 B2
(45) Date of Patent: Sep. 21, 2010

(54) SYSTEM AND METHOD FOR CREATING MIXED IMAGE FROM DUAL-ENERGY CT DATA

(75) Inventors: Lifeng Yu, Rochester, MN (US); Cynthia H. McCollough, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 12/276,501

(22) Filed: Nov. 24, 2008

(65) Prior Publication Data

US 2009/0135994 A1 May 28, 2009

Related U.S. Application Data

(60) Provisional application No. 60/989,875, filed on Nov. 23, 2007.

(51) Int. Cl.
*A61B 6/00* (2006.01)
(52) U.S. Cl. .................... 378/5; 378/4; 378/9
(58) Field of Classification Search .......... 378/5, 378/9, 4
See application file for complete search history.

(56) References Cited

U.S. PATENT DOCUMENTS

| | | | | |
|---|---|---|---|---|
| 4,463,375 | A * | 7/1984 | Macovski | 378/98.12 |
| 5,115,394 | A | 5/1992 | Walters | |
| 2002/0094062 | A1 * | 7/2002 | Dolazza et al. | 378/98.9 |
| 2003/0147497 | A1 * | 8/2003 | Avinash | 378/98.9 |
| 2004/0101104 | A1 * | 5/2004 | Avinash et al. | 378/98.12 |
| 2005/0163283 | A1 * | 7/2005 | Bruder et al. | 378/98.11 |
| 2006/0109949 | A1 * | 5/2006 | Tkaczyk et al. | 378/4 |
| 2006/0280281 | A1 * | 12/2006 | Flohr et al. | 378/5 |
| 2006/0285634 | A1 * | 12/2006 | Toth | 378/16 |

\* cited by examiner

*Primary Examiner*—Edward J Glick
*Assistant Examiner*—Alexander H Taningco
(74) *Attorney, Agent, or Firm*—Quarles & Brady LLP (57) ABSTRACT

A system and method for creating a combined or mixed-energy image using both low- and high-energy CT data sets acquired using a dual-energy CT system. The low- and high-energy datasets are mixed using desired weighting factors to mimic a "single-energy" image. The low-energy dataset provides data with improved contrast enhancement, but with increased noise level. The high-energy dataset provides data with lower contrast enhancement, but with better noise properties. By combining the low- and high-energy datasets in accordance with the present method, the resulting mixed-energy images utilize the information of full dose of radiation used in the dual-energy scan. A plurality of weighting metrics can be selected, including patient size, dose partitioning, or image quality, to determine the desired weighting factors based on the weighting metrics. By selecting the proper weight factors, image noise can be reduced and/or the contrast to noise ratio can be increased in the mixed-energy image.

16 Claims, 7 Drawing Sheets

SYSTEM AND METHOD FOR CREATING MIXED IMAGE FROM DUAL-ENERGY CT DATA

CROSS-REFERENCE TO RELATED APPLICATIONS

This application is based on, incorporates herein by reference, and claims the benefit of provisional application Ser. No. 60/989,875, filed Nov. 23, 2007, and entitled "SYSTEM AND METHOD FOR CREATING MIXED IMAGE FROM DUAL-ENERGY CT DATA."

STATEMENT REGARDING FEDERALLY SPONSORED RESEARCH

Not applicable.

FIELD OF THE INVENTION

The present invention relates to computed tomography (CT) imaging systems and, more particularly, to a method for creating a mixed-energy, composite image that is similar in quality to an image commonly created using single-energy CT using data acquired at more than one x-ray energy level.

BACKGROUND OF THE INVENTION

In a current computed tomography system, an x-ray source projects a fan-shaped beam that is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

Dual-source or dual-energy CT systems have two separate x-ray sources and associated detector arrays, which rotate together in the gantry during a scan. The x-ray sources may be operated at different energy levels to acquire two image data sets from which a low energy and a high energy image may be reconstructed.

Dual-energy CT systems are typically used for specific applications, such as bone removal, iodine quantification, and material characterization. In these applications, the two data sets at low- and high-energy are acquired simultaneously, which eliminates the mis-registration problems. Many dual-energy processing techniques, either before or after the reconstruction, can thus be applied on the low- and high-energy data sets to obtain basis material-specific information.

In addition to the "specialized" images that are generated in these applications, another set of images is often generated from the dual-energy data to provide images for "traditional" diagnostic purposes. Since "traditional" diagnostic images are typically generated using a single-energy CT system, an operator typically selects either the low- or high-energy dataset to generate a set of images. However, this method creates images with reduced image quality when compared with an image generated from a "single-energy" data acquisition because each of the image data sets from the dual-energy scan is generated with approximately one-half of the radiation dose of the corresponding single-energy scan.

Accordingly, some operators have been known to perform a second, single-energy data acquisition from which to generate the desired images. However, this has a number of drawbacks. First, it subjects the patient to additional doses of radiation. Second, the dual-energy datasets and the single-energy datasets are not temporally related and may be mis-registered.

Therefore, it would be desirable to have a system and method for providing an operator with a variety of images that convey the advantageous information included in both dual-energy images and single-energy images without the need to expose the subject to multiple imaging acquisitions and the separate radiation doses associated with each acquisition. Furthermore, it would be desirable that such a system and method reduce the likelihood of temporal and spatial mis-registrations.

SUMMARY OF THE INVENTION

The present invention provides a system and method for creating a combined or mixed image using both low- and high-energy CT data sets acquired using a dual-energy CT system. Accordingly, the present invention mixes the low- and high-energy datasets to mimic a "single-energy" image. The low-energy dataset provides data with improved contrast enhancement, but with increased noise level. The high-energy dataset provides data with lower contrast enhancement, but with better noise properties. By properly combining the low- and high-energy datasets, mixed-energy images can be created that utilize the information provided by the full dose of radiation used in the dual-energy scan to generate images having an image quality that is better than either of the low- and high-energy images and more closely matched to that of a single-energy image. Hence, the mixed-energy images are suitable for clinical anatomical analysis that, previously, could only utilize single-energy images.

In accordance with one embodiment a linear, weighted combination is used to generate the mixed-energy images. In accordance with this method, the low- and high-energy images are linearly-combined together with two normalized weighting factors applied globally on each of the dual-energy datasets. The optimization of the image quality involves the determination of the weighting factors that yield the best image quality. Depending on the diagnostic task, the best image quality of the mixed images will have either the lowest noise level or the highest contrast-to-noise ratio (CNR) possible using the low- and high-energy images. The desired weighting factors that are used to generate the mixed-energy images are determined according to this basis. In addition, because the noise and contrast properties of the low- and high-energy images both depend on the patient size and the radiation dose partitioning between the two energies, the desired weighting factors rely on these additional parameters.

Various other features of the present invention will be made apparent from the following detailed description and the drawings.

DETAILED DESCRIPTION OF THE INVENTION

Figure 1:
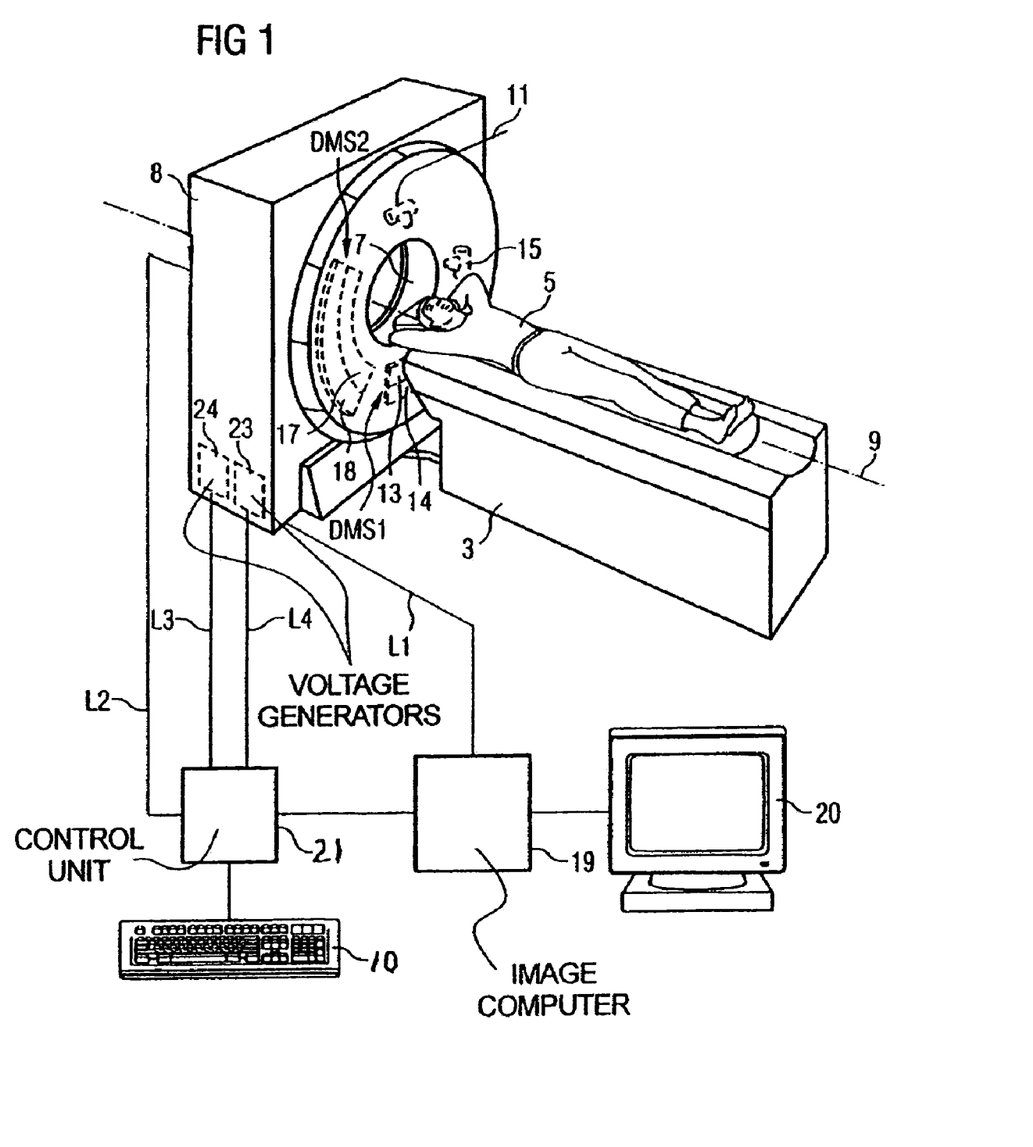
FIG. 1 is a block diagram of a dual-energy CT system for use with the present invention.

Referring to FIG. 1, the CT system 1 includes a patient table 3 for supporting and positioning an examination subject 5. The region of interest in the patient 5 can be inserted into an opening 7 in a housing 8 of the CT system 1 by means of a movable table top included with the patient table 3. Inside the housing 8, a gantry (not visible) is mounted so as to be rotated with high speed around a rotation axis 9 running through the subject 5. Moreover, for a spiral, or helical, scan a continuous axial feed is effected with by adjusting the patient table 3. A user interface 10 is provided to control operation of the CT system 1 by a doctor or an assistant.

Two data acquisition systems are mounted on the gantry. A first acquisition system has an x-ray tube as a first radiator 11 and a first data acquisition unit DMS 1 formed as a multi-row, x-ray detector array as a first detector 13. A second acquisition system has a separate x-ray tube as a second radiator 15 and furthermore a second data acquisition unit DMS 2 formed as a separate multi row x-ray detector array as a second detector 17. The arrangement of the two radiators 11, 15 and the two detectors 13, 17 on the gantry is fixed during the operation of the CT system 1, such that their relative separations are constant during operation.

The x-ray detector arrays are fashioned on a base of an electronically readable scintillator ceramic, known as a UFC ceramic. Surface detectors, for example with 256 or more lines, alternatively can be used. The electronic signals generated by the x-ray detector arrays are conditioned in respective downstream electronic data processing units 14 and 18 that, together with the respective associated detector 13 and 17, form the data acquisition units DMS 1 and DMS 2. In the data processing units 14 and 18, the electronic signals are integrated and digitized.

The projection data of both acquisition systems are supplied via wiper rings or an optical transmission system to the stationary part of the gantry, and then to an image computer 19. In the image computer 19, the acquired projection views are processed using an image reconstruction method into a CT image that can be displayed on a display device 20. The image computer 19 is fashioned such that the reconstruction of an image can be implemented separately using projection data or raw data from each acquisition systems. As will be described in more detail below, these separate images can then processed to produce a single, mixed-energy image.

The CT system 1 is controlled using the control unit 21 that is connected with the image computer 19 and with the user interface 10. The control unit 21 is also connected with the data processing units 14 and 18 via a data transmission line L1. Moreover, the control unit 21 operates through lines L3, L4 two voltage generators 23, 24 that respectively supply the x-ray tubes 11 and 15 with energy.

Figure 2:
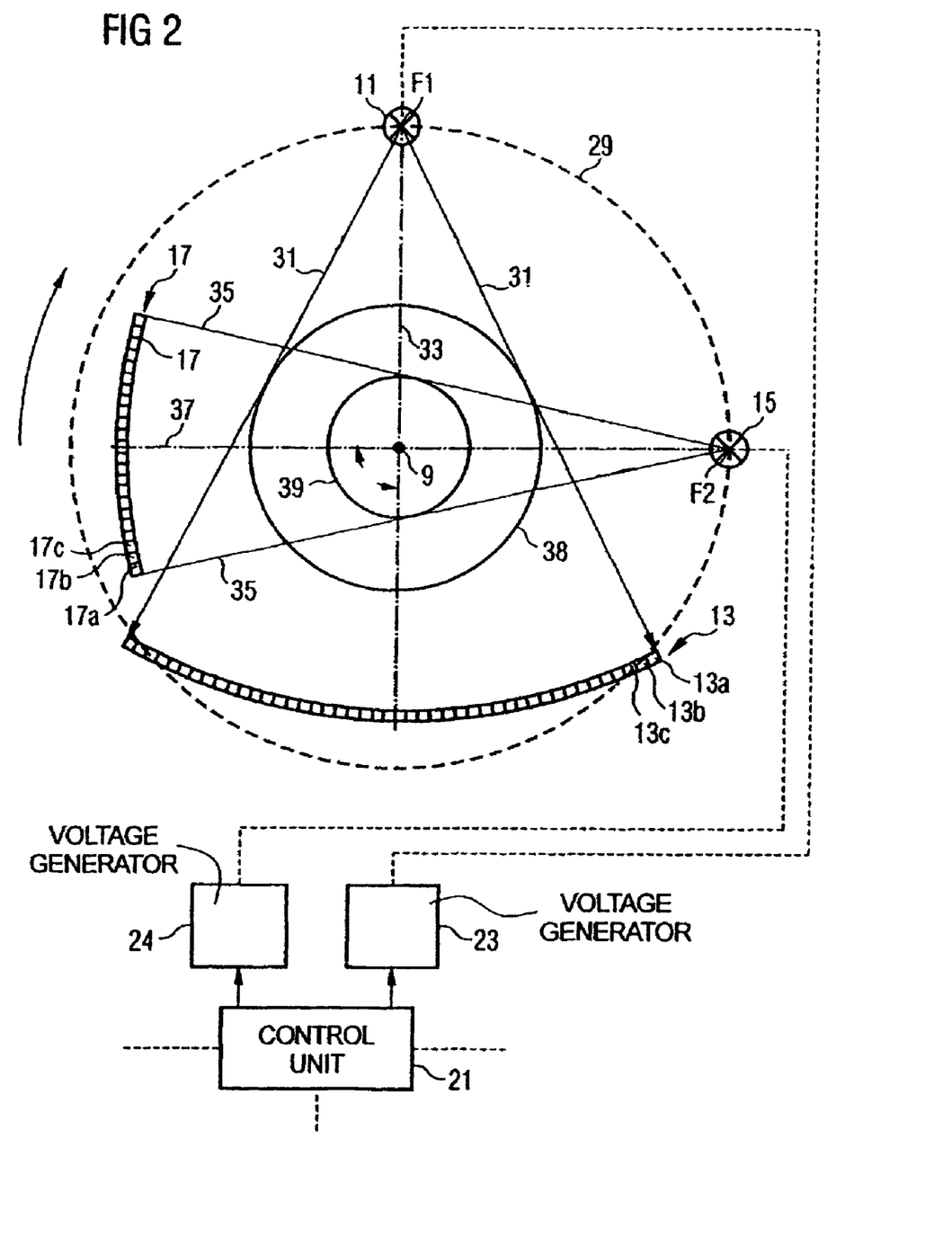
FIG. 2 is a schematic representation of the source and detector system of FIG. 1.

Turning now to FIG. 2, both acquisition systems of FIG. 1 are shown in detail. In particular, both x-ray tubes 11, 15 and respective focuses, F1 and F2, rotate in the arrowed direction on a common rotation path 29 around a rotational z-axis 9, which is perpendicular to the plane of the drawing. The x-ray tubes 11, 15 alternately radiate x-ray fan beams that are respectively shown with edge rays 31 and 35 and a middle rays 33 and 37. During the respective radiation, raw data is generated from different projection angles for a subsequent image reconstruction. In the cross-section of FIG. 2, only one line of the respective detectors 13 and 17, with detector elements 13a, 13a, 13c and 17a, 17a, 17c, and so on, is shown. The length of each detector 13 and 17 is curved around the respective focus F1, F2, of the associated radiators 11 and 15, and are different, such that, in the representation of FIG. 2, detectable x-ray beams of different sizes arise for the two acquisition systems, and maximum measurement fields 38 and 29 of different sizes result.

The control unit 21 acts on the voltage generators 23, 24 such that the x-rays tubes or radiators 11, 15 alternately radiate. More importantly, the control unit 21 separately controls the voltage applied to each x-ray tube 11 and 15 such that two images may be acquired simultaneously from a region of interest in the patient at two different energy levels.

In dual-source, dual-energy CT, the images reconstructed from the low- and high-energy scans, typically at 80 kV and 140 kV, respectively, are usually combined together to provide a single set of images. Different from dual-energy processing techniques that provide material-specific information from the dual-energy scan, the following method provides mixed-energy images created with the purpose of offering a single set of images similar to that would be obtained from a single-energy scan, typically at 120 kV, for the same total radiation dose. Thus, as referred to herein, a "mixed-energy image" refers to an image that is created using images reconstructed from low- and high-energy scans to have an image quality that is similar to that of a single-energy image acquired using a medium-energy scan that is less than the high-energy scan and greater than the low-energy scan. Hence, a mixed-energy image is readily distinguishable from traditional dual-energy images that are created or combined for purposes of material decomposition. Both the mixed-energy images and the dual-energy processed images add value to the clinical examination but have different clinical purposes.

In accordance with the present invention, the image quality of linearly-mixed images is dependent on four main factors. The first factor is the total radiation dose and dose partitioning between the low- and high-energy scans. The second factor is the patient size. The third and fourth factors are the weighting factors used in the linear combination and the image quality metrics to be optimized (noise or CNR).

Although the ultimate determination of image quality is diagnostic task and observer specific, an image quality metric, such as noise level or CNR, is an objective evaluation metric. Specifically, it is contemplated that for objective evaluation or a baseline starting point image, quality may be optimized for two different metrics. Specifically, image quality may be optimized for the lowest noise level or the highest CNR.

The mixed image I is given by:

$$I = w_L I_L + w_H I_H \qquad \text{Eqn. 1;}$$

where $I_i$ (i=L, H) denotes the low and high-energy images, $w_i$ (i=L, H) is the weighting factor for the low and high-energy images and $w_L + w_H = 1$. Herein, the subscript (i=L, H) represents the low and high-energy scans, respectively.

The standard deviations of CT numbers in the background and iodine signal regions is defined as $\sigma_{i,b}$, and $\sigma_{i,s}$, (i=L, H). The subscripts b and s represent "background" and "signal", respectively. The iodine contrast (the absolute difference of the CT numbers between the signal region and background region) for the low- and high-energy images is denoted by $C_i$ (i=L,H).

It can be shown that the weighting factor for the lowest background noise level in the mixed image and the corresponding noise level are given by:

$$w_L(\sigma_{min}) = \frac{\sigma_{H,b}^2}{\sigma_{L,b}^2 + \sigma_{H,b}^2}; \qquad \text{Eqn. 2}$$

and $$\sigma_{min} = \frac{\sigma_{L,b}\sigma_{H,b}}{\sqrt{\sigma_{L,b}^2 + \sigma_{H,b}^2}}. \qquad \text{Eqn. 3}$$

It can also be shown that the weighting factor for the highest CNR in the mixed image and the corresponding maximum CNR are given by:

$$w_L(CNR_{max}) = \frac{C_L(\sigma_{H,s}^2 + \sigma_{H,b}^2)}{C_L(\sigma_{H,s}^2 + \sigma_{H,b}^2) + C_H(\sigma_{L,s}^2 + \sigma_{L,b}^2)}; \qquad \text{Eqn. 4}$$

and $$CNR_{max} = \sqrt{\frac{2C_L^2}{(\sigma_{L,s}^2 + \sigma_{L,b}^2)} + \frac{2C_H^2}{(\sigma_{H,s}^2 + \sigma_{H,b}^2)}}. \qquad \text{Eqn. 5}$$

For each dual-energy image dataset, an iodine signal, a background signal, and a noise signal in the background can be measured and averaged over adjacent images, for example, six images. The weighting factors can then be adjusted to yield a desired image. For example, weighting factors that yield the lowest noise level or highest CNR can be calculated, respectively, based upon Equations 2 and 4. The corresponding noise level and CNR can be calculated from the mixed images, and this procedure can then be repeated for each dose partition and patient size.

Maximizing CNR

Figure 3A:
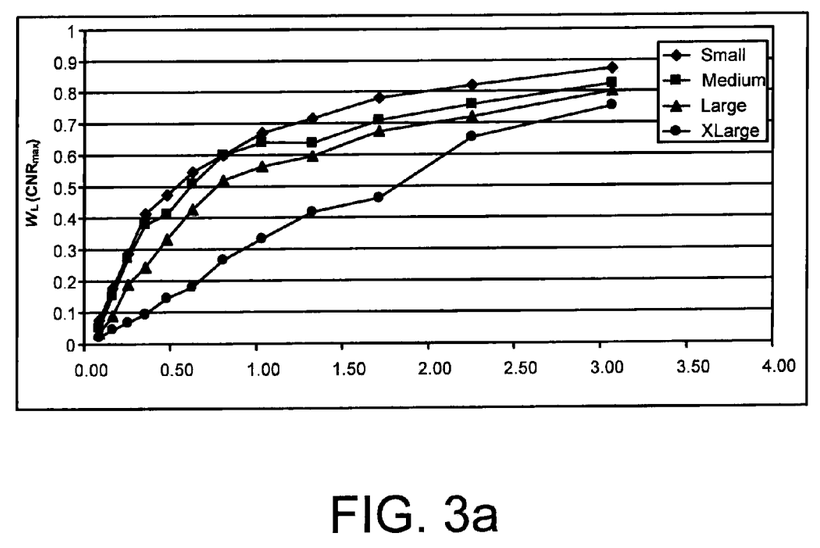
FIGS. 3a and 3b are graphs of weighting factors for maximal CNR, $W_L(CNR_{max})$, as functions of the dose ratio between the 80 kV and 140 kV, $D_{140}^{80}$, for four phantom sizes.
Figure 3B:
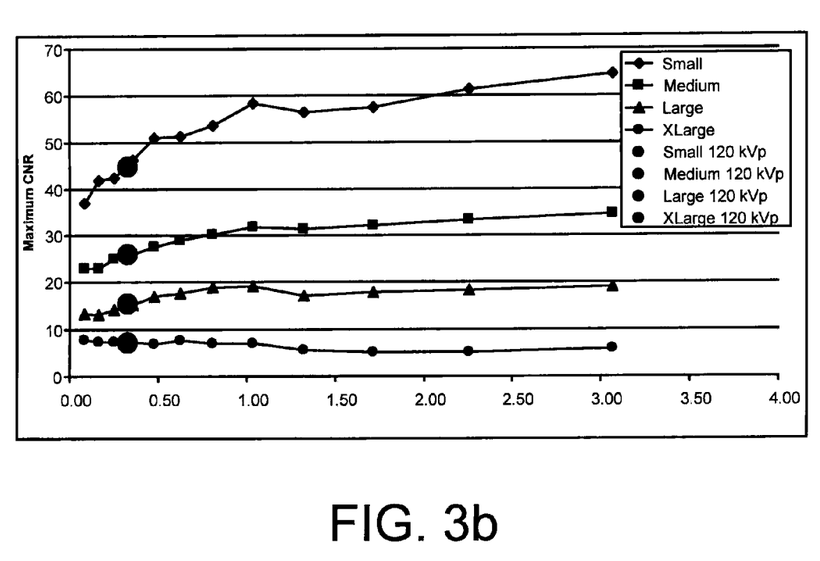
Figure 4A:
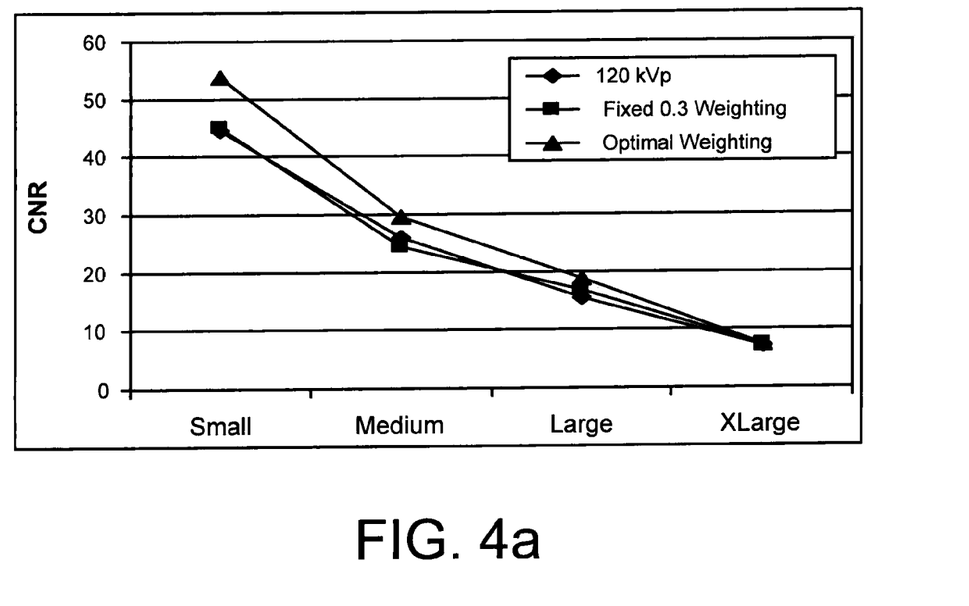
FIGS. 4a and 4b are graphs of the CNR corresponding to the weighting factors of FIGS. 3a and 3b shown as functions of the dose ratio between 80 kV and 140 kV for the four phantom sizes.
Figure 4B:
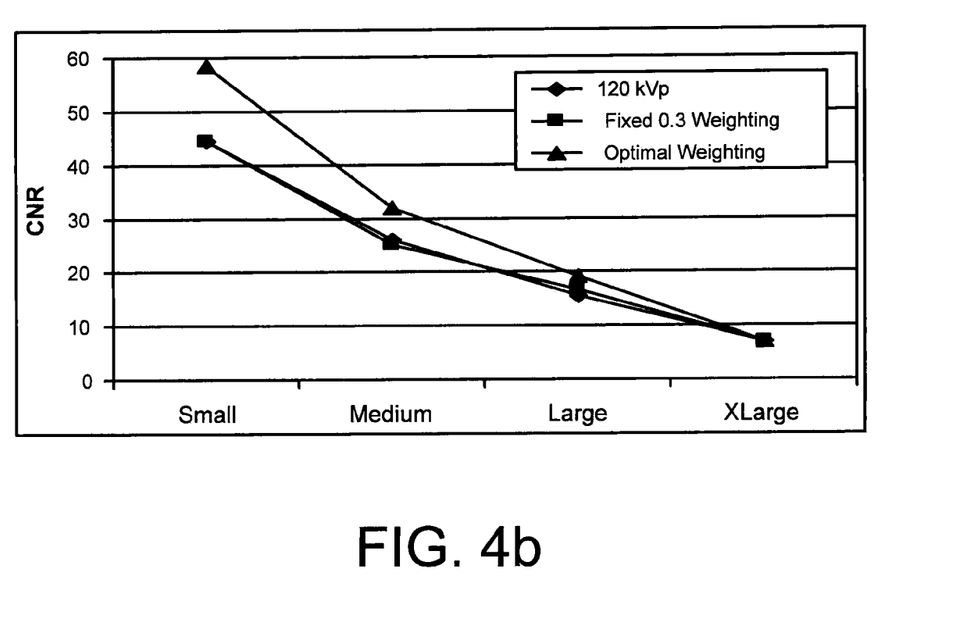

Referring now to FIGS. 3a and 3b, graphs of weighting factors for maximal CNR, $w_L(CNR_{max})$, as functions of the dose ratio between the 80 kV and 140 kV, $D_{140}^{80}$, for four phantom sizes are illustrated. The total radiation dose was 17.3 mGy in all cases. The weighting factor was obtained by using Equation 4, which yields the highest CNR for the given phantom size and dose ratio. The corresponding CNRs as functions of the dose ratio between 80 kV and 140 kV for the four phantom sizes are displayed in FIGS. 4a and 4b. For both of these figures and all the other figures below, the weighting factor refers to the coefficient applied to the 80 kV images, the weighting factor applied on 140 kV images was 1 minus this weighting factor. Also displayed in FIGS. 4a and 4b is the CNR in the single-energy images for the four phantom sizes and same radiation dose.

It is clear that the weighting factor that yields the highest CNR is highly dependent on the patient/phantom size and the dose partition between low- and high-energy images. With the increase of the radiation dose at 80 kV, the weighting factor increases for all of the patient/phantom sizes. With the increase of the patient/phantom size, the weighting factor decreases. For a dose ratio of 0.81 that is typically used clinically, the preferred weighting factors are 0.60, 0.60, 0.52, and 0.26 for small, medium, large, and extra large patient/phantom sizes, respectively. For a dose ratio of 1.03, the preferred weighting factors were 0.67, 0.63, 0.56, and 0.33.

It can be seen that the CNRs in the mixed images with a fixed 0.3 weighting factor are very similar to that in the 120 kV images for all the patient/phantom sizes. The optimal weighting factors yield better CNRs than does the fixed 0.3 weighting factor as well as the 120 kV images, particularly when the phantom size is small.

Minimizing Image Noise

Figure 5A:
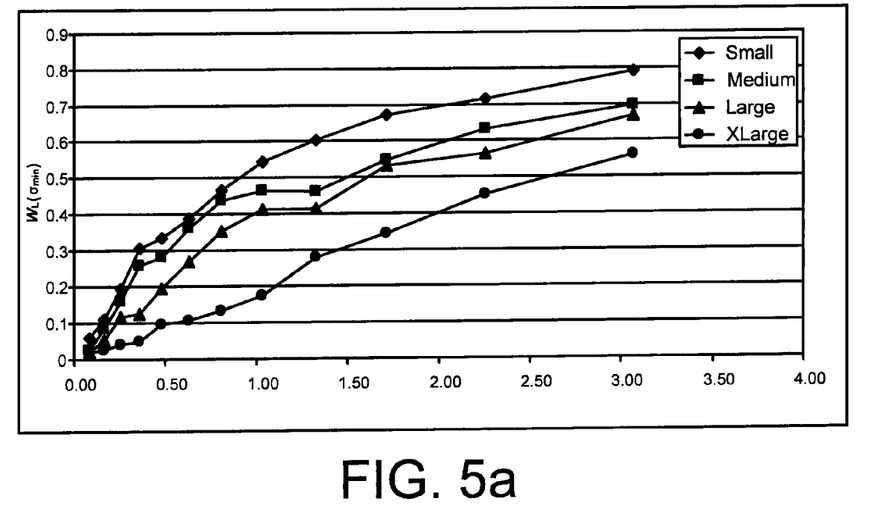
FIGS. 5a and 5b are graphs of the weighting factors for minimal noise levels as functions of the dose ratio between 80 kV and 140 kV for four phantom sizes.
Figure 5B:
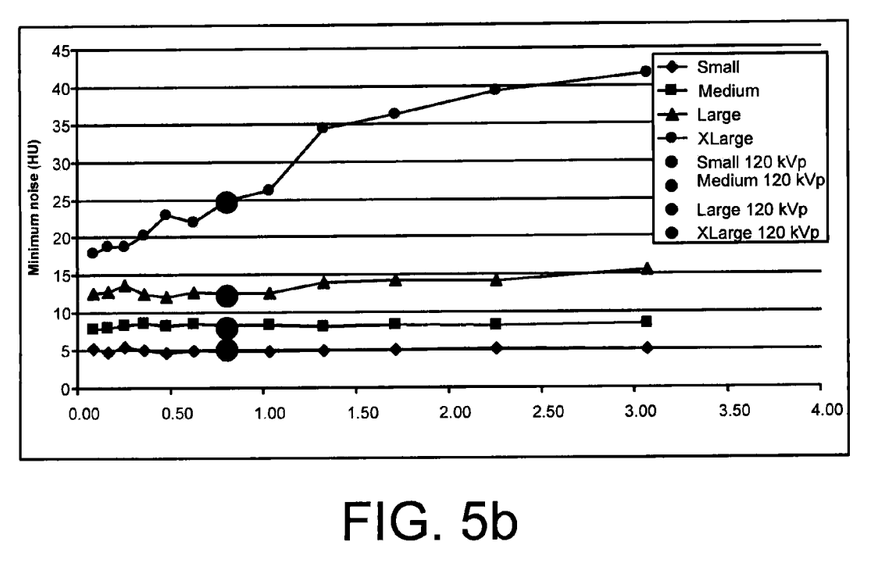

For each of the datasets acquired at a given dose ratio and patient/phantom size, the optimal weighting factors that yield the lowest noise in the mixed image can also be obtained. FIGS. 5a and 5b are graphs of the weighting factors for minimum noise as functions of dose ratio between 80 kV and 140 kV for the four phantom sizes.

Figure 6A:
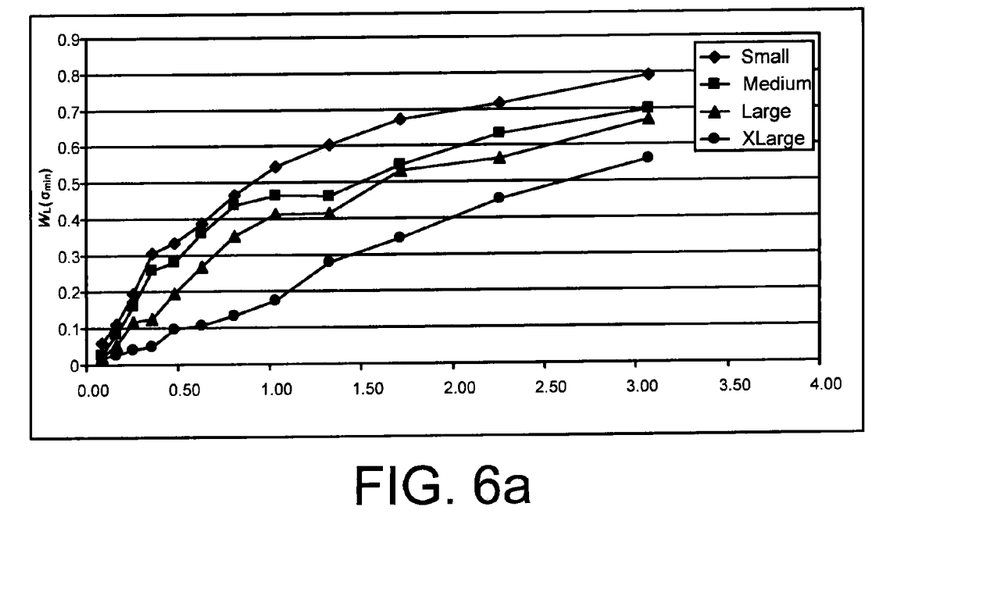
FIGS. 6a and 6b are graphs of the minimum noise values as functions of the dose ratio between 80 kV and 140 kV for four phantom sizes.
Figure 6B:
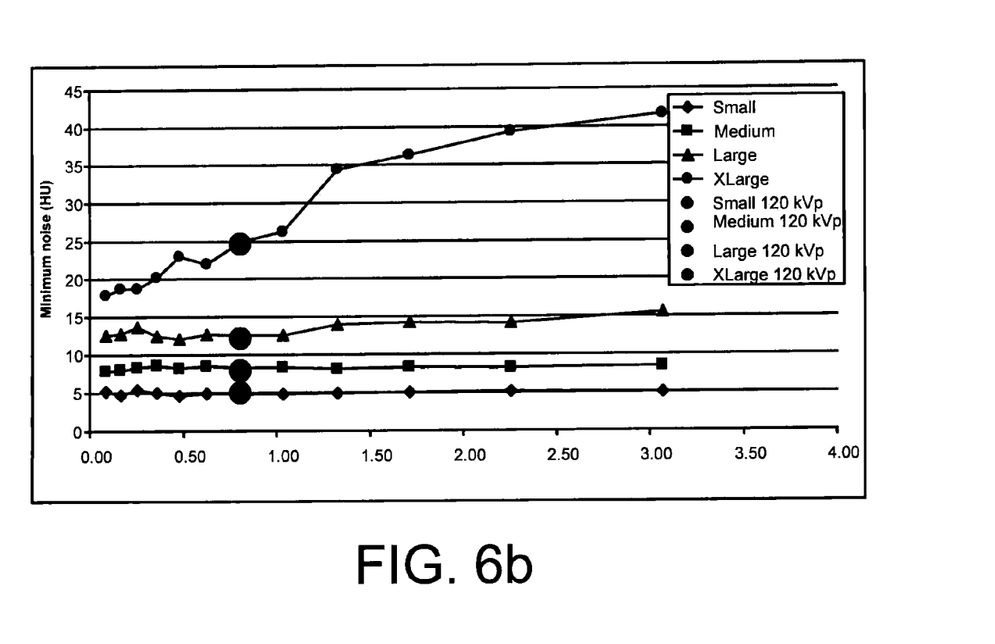

The total radiation dose is 17.3 mGy. The optimal weighting factor was obtained by using Equation 2, which yields the lowest noise level for the given phantom size and dose ratio. The corresponding minimum noise levels as functions of the four phantom sizes are shown in FIGS. 6a and 6b. Also displayed in FIGS. 6a and 6b is the noise in the single-energy images (120 kV) for the four phantom sizes at the same total amount of radiation dose.

The weighting factor ($w_L(\sigma_{min})$) that yields the lowest noise level is highly dependent on the patient/phantom size and the dose partition. With the increase of the radiation dose at 80 kV, $w_L(\sigma_{min})$ increases for all phantom sizes. With increasing phantom size, $w_L(\sigma_{min})$ decreases. Furthermore, the minimum noise is less dependent on patient/phantom size and the dose partition compared to the maximum CNR. When the patient size is extra large, the noise level is higher when the dose proportion of 80 kV becomes bigger. For other patient/phantom sizes, the minimum noise level is relatively stable.

Also, the noise level in single-energy images at 120 kV with the same total dose is very close to that in the mixed images for small, medium, and large patient/phantom sizes. For the extra large patient size, the noise varies considerably with the change of dose partition. The noise level of 120 kV images is similar to that in the mixed images with dose ratio of 0.81. Above 0.81, the 120 kV has a lower noise level. Below 0.81, the 120 kV has a higher noise level.

As described above, the dual-energy mixed images can achieve similar or even better CNR than the single-energy images using the same total radiation dose. When the dose ratio between 80 kV and 140 kV is larger than 0.33, the mixed images have better CNR than the single-energy images for the studied small, medium, and large phantoms. For the extra-large patient/phantom, the CNRs are relatively insensitive to the dose partitioning between 80 kV and 140 kV, with slightly smaller CNR when the dose proportion at 80 kV increases.

Therefore, for smaller patient size in dual-energy scan, the increase of the dose proportion at 80 kV leads to an increase of the contrast enhancement without much compromise of the noise, which leads to better CNR when the dose ratio between 80 kV and 140 kV becomes larger and larger. In contrast, for bigger patient sizes, the increase of the dose proportion at 80 kV involves a substantial compromise of the noise, which cancels the benefit of the increased contrast enhancement and leads to a similar or even worse CNR.

Accordingly, increasing the dose proportion of 80 kV in dual-energy scan for smaller patient sizes would be beneficial for the image quality in the mixed images. This is generally correct except with consideration of two limitation factors.

First, the scanning speed may limit the maximum radiation dose achievable at 80 kV. For example, the maximum tube current on the current scanner (Definition) is 500 mA. For a rotation time of 0.5 second and a helical pitch of 0.45, the maximum effective mAs is only 555 mAs. Further reducing the rotation time would increase the maximum effective mAs; however, the scanning time would be unacceptably long for most studies.

Second, other dual-energy processing techniques require a balance of noise level between 140 kV and 80 kV. Optimization of the image quality in the mixed-energy images is not the only goal of the dual-energy study. Mainly due to these two reasons, clinically viable dose ratio between 80 kV and 140 kV is often less than 1. For a given dose ratio, the weighting factor for generating the mixed images can still be optimized by adapting it to the patient size.

Figure 7:
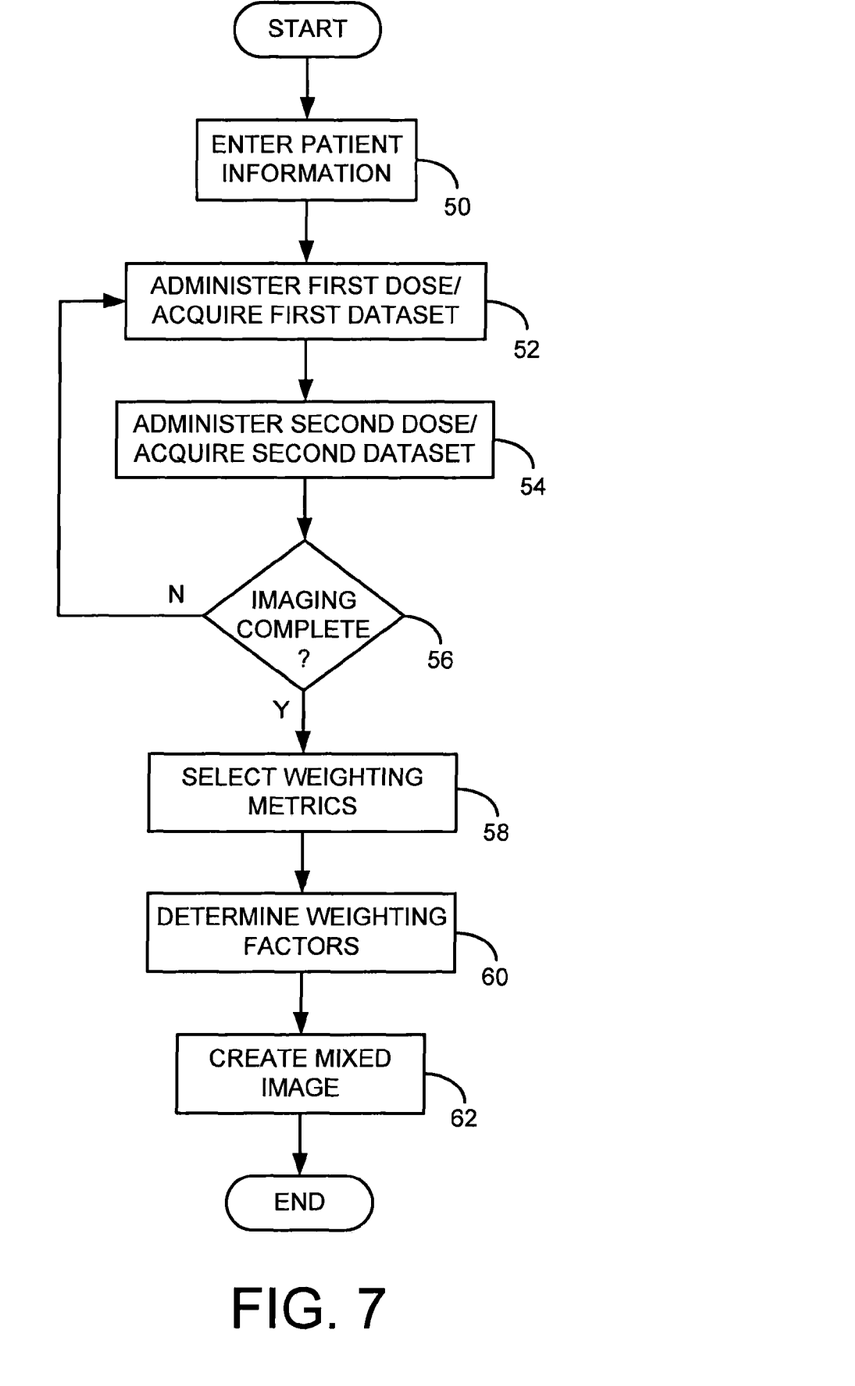
FIG. 7 is a flow chart setting forth the steps for creating a mixed image in accordance with the present invention.

Referring now to FIG. 7, a method for creating a mixed image begins at process block 50 by entering patient information. The patient information may include typical identification information but, in accordance with the present invention, also includes data that can later be used to determine weighting metrics, such as patient size. At process block 52, the method continues by initiating the imaging process by administering the first radiation dose/acquiring data for the first dataset. Since dual-energy CT imaging process typically interleave radiation doses, following thereafter at process block 54 the second radiation dose is administered and data for the second dataset is acquired.

This process continues until the imaging process is complete and, at process block 58, weighting metrics can be selected. Alternatively, it is contemplated that the weighting metrics may be selected prior to data acquisition; however, it is preferable to select the weighting metrics following data acquisition because, in some cases, the acquired data may be utilized to aid in selecting the weighting metrics. As described above, the present invention is capable of utilizing a variety of weighting metrics, including patient size, dose partitioning, desired image quality, and the like.

Once the weighting metrics are selected at process block 58 according to the considerations described above, the weighting factors needed to meet the criteria established by the weighting metrics is determined at process block 60. In the manner described above, the weighting factors can be selected to achieve such objectives as minimizing image noise or maximizing CNR. Once the weighting factors have been determined at process block 60, a mixed image is created using the weighting factors and the process ends.

Therefore, the present invention provides a method for providing a mixed-energy image. Furthermore, the present invention provides a method for evaluating and adjusting the image quality of the mixed images created from dual-energy scans using a dual-source CT scanner when compared with the images acquired from single-energy scans for the same total amount of radiation dose.

Depending on the patient size, dose partitioning, and image quality metrics to be optimized (CNR or noise), the optimal weighting factors may vary. The present invention provides a system and method for the determination of optimal weighting factors as a function of patient size and dose partition between low- and high-energies. The results demonstrate that similar noise and similar or improved CNR relative to 120 kV images can be achieved from the dual-energy images by creating mixed-energy images in accordance with the present invention. Hence, the present invention provides a system and method to yield both dual-energy images and mixed-energy images for the same total amount of radiation dose as required for only the dual-energy images over a wide range of patient sizes.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

We claim:

1. A method for generating a mixed-energy CT image comprising the steps of:
    a) administering a first dose of x-rays at a first energy to acquire a first image dataset;
    b) administering a second dose of x-rays at a second energy that is different from the first energy to acquire a second image dataset;
    c) selecting at least one of a plurality of weighting metrics including at least one of patient size, dose partitioning, and image quality;
    d) determining at least one desired weighting factor based on the weighting metrics; and
    e) creating a mixed-energy image from the first image dataset and the second image data set based on the at least one desired weighting factor.

2. The method of claim 1 wherein step d) includes weighting the weighting metrics based on the at least one desired weighting factor.

3. The method of claim 1 wherein step e) includes reconstructing a low-energy image and a high-energy image from the first image dataset and the second image dataset, respectively.

4. The method of claim 3 wherein the mixed-energy image, I, is given by $I = w_L I_L + w_H I_H$, where $I_i$ (i=Low-energy image (L), High-energy image (H)) denotes the low and high-energy images, $w_i$ (i=L, H) is the weighting factor for the low and high-energy images, and $w_L + w_H = 1$.

5. The method of claim 4 wherein the at least one desired weighting factor is selected to minimize image noise in the mixed-energy image.

6. The method of claim 5 wherein the weighting factor is given by $$w_L(\sigma_{min}) = \frac{\sigma_{H,b}^2}{\sigma_{L,b}^2 + \sigma_{H,b}^2} \text{ and } \sigma_{min} = \frac{\sigma_{L,b}\sigma_{H,b}}{\sqrt{\sigma_{L,b}^2 + \sigma_{H,b}^2}},$$

where $\sigma_{i,b}$, and $\sigma_{i,s}$, (i=L, H) is the standard deviations of CT numbers in background, b, and iodine signal, s.

7. The method of claim 4 wherein the at least one desired weighting factor is selected to maximize contrast to noise ratio in the mixed image.

8. The method of claim 7 wherein the weighting factor is given by $$w_L(CNR_{max}) = \frac{C_L(\sigma_{H,s}^2 + \sigma_{H,b}^2)}{C_L(\sigma_{H,s}^2 + \sigma_{H,b}^2) + C_H(\sigma_{L,s}^2 + \sigma_{L,b}^2)} \text{ and}$$

$$CNR_{max} = \sqrt{\frac{2C_L^2}{(\sigma_{L,s}^2 + \sigma_{L,b}^2)} + \frac{2C_H^2}{(\sigma_{H,s}^2 + \sigma_{H,b}^2)}},$$

where $C_i$ (i=L, H) is iodine contrast in the low- and high-energy images found as an absolute difference of CT numbers between signal region and background region in the low-energy and high-energy images, where an iodine signal, a background signal, and a noise signal in the background are measured and averaged over adjacent images.

9. The method of claim 1 wherein steps a) and b) are performed using separate radiation sources having separate focuses.

10. A method for generating a mixed-energy CT image comprising the steps of:
   a) administering a first dose of x-rays at a first energy to acquire a portion of a first image data set;
   b) administering a second dose of x-rays at a second energy that is different from the first energy to acquire a portion of a second image data set;
   c) repeating steps a) and b) to acquire the first image dataset set and the second image dataset, respectively;
   d) reconstructing a high-energy image from the first image dataset and a low-energy image from the second image dataset;
   e) selecting at least one of a plurality of weighting metrics including at least one of patient size, dose partitioning, and image quality;
   f) determining at least one desired weighting factor based on the weighting metrics; and
   g) performing a linear, weighted combination of the low-energy image and the high-energy image based on the at least one desired weighting factor to create a mixed-energy image.

11. The method of claim 10 wherein the mixed image, I, is given by $I = w_L I_L + w_H I_H$, where $I_i$ (i=L, H) denotes the low and high-energy images, $w_i$ (i=L, H) is the weighting factor for the low and high-energy images, and $w_L + w_H = 1$.

12. The method of claim 11 wherein the at least one desired weighting factor is selected to minimize image noise in the mixed-energy image.

13. The method of claim 12 wherein the weighting factor is given by $$w_L(\sigma_{min}) = \frac{\sigma_{H,b}^2}{\sigma_{L,b}^2 + \sigma_{H,b}^2} \text{ and } \sigma_{min} = \frac{\sigma_{L,b}\sigma_{H,b}}{\sqrt{\sigma_{L,b}^2 + \sigma_{H,b}^2}},$$

where $\sigma_{i,b}$, and $\sigma_{i,s}$, (i=L, H) is the standard deviations of CT numbers in background, b, and iodine signal, s.

14. The method of claim 11 wherein the at least one desired weighting factor is selected to maximize contrast to noise ratio in the mixed image.

15. The method of claim 14 wherein the weighting factor is given by $$w_L(CNR_{max}) = \frac{C_L(\sigma_{H,s}^2 + \sigma_{H,b}^2)}{C_L(\sigma_{H,s}^2 + \sigma_{H,b}^2) + C_H(\sigma_{L,s}^2 + \sigma_{L,b}^2)} \text{ and}$$

$$CNR_{max} = \sqrt{\frac{2C_L^2}{(\sigma_{L,s}^2 + \sigma_{L,b}^2)} + \frac{2C_H^2}{(\sigma_{H,s}^2 + \sigma_{H,b}^2)}},$$

where $C_i$ (i=L, H) is iodine contrast in the low- and high-energy images found as an absolute difference of CT numbers between signal region and background region in the low-energy and high-energy images, where an iodine signal, a background signal, and a noise signal in the background are measured and averaged over adjacent images.

16. The method of claim 10 wherein steps a) and b) are performed using separate radiation sources having separate focuses.

* * * * *